(12) United States Patent
Madix et al.

(10) Patent No.: US 8,889,908 B2
(45) Date of Patent: Nov. 18, 2014

(54) SILVER-CATALYZED SYNTHESIS OF AMIDES FROM AMINES AND ALDEHYDES

(75) Inventors: Robert J. Madix, Lexington, MA (US); Ling Zhou, Cambridge, MA (US); Bingjun Xu, Cambridge, MA (US); Cynthia M. Friend, Lexington, MA (US); Cassandra G. Freyschlag, Colorado Springs, CO (US)

(73) Assignee: President and Fellows of Harvard College, Cambridge, MA (US)

( * ) Notice: Subject to any disclaimer, the term of this patent is extended or adjusted under 35 U.S.C. 154(b) by 187 days.

(21) Appl. No.: 13/575,150

(22) PCT Filed: Jan. 25, 2011

(86) PCT No.: PCT/US2011/022434
§ 371 (c)(1), (2), (4) Date: Dec. 7, 2012

(87) PCT Pub. No.: WO2011/091427
PCT Pub. Date: Jul. 28, 2011

(65) Prior Publication Data
US 2013/0079556 A1    Mar. 28, 2013

Related U.S. Application Data

(60) Provisional application No. 61/336,673, filed on Jan. 25, 2010.

(51) Int. Cl.
*C07C 231/10* (2006.01)
*C07C 233/05* (2006.01)

(52) U.S. Cl.
USPC ........................................................ 564/215

(58) Field of Classification Search
USPC .......................................... 564/189, 190, 215
See application file for complete search history.

(56) References Cited

U.S. PATENT DOCUMENTS

| | | | |
|---|---|---|---|
| 4,219,509 | A | 8/1980 | Nielsen et al. |
| 6,339,157 | B1 | 1/2002 | Bei et al. |
| 2002/0055638 | A1* | 5/2002 | Riermeier et al. ............ 546/189 |
| 2009/0112005 | A1 | 4/2009 | Milstein et al. |

OTHER PUBLICATIONS

Tillack et al, Eur. J. Org. Chem., 2001, 523-528.*
Bare et al., "Generation of atomic oxygen on Ag(111) and Ag(110) using NO2: a TPD, LEED, HREELS, XPS and NRA study," Surf Sci. 342:185-98 (1995).
Beller et al., "Progress in hydroformylation and carbonylation," J Mol Catal A:Chem. 104:17-85 (1995).
Ghosh et al., "Direct amide synthesis from alcohols and amines by phosphine-free ruthenium catalyst systems," Adv Synth Catal. 351:2643-9 (2009).
Gong et al., "Selective oxidation of propylamine to propionitrile and propionaldehyde on oxygen-covered gold," Chem Commun (Camb). (7):761-3 (2009).
Gunanathan et al., "Direct synthesis of amides from alcohols and amines with liberation of H2," Science. 317(5839):790-2 (2007).
Humphrey et al., "Chemical Synthesis of Natural Product Peptides: Coupling Methods for the Incorporation of Noncoded Amino Acids into Peptides," Chem Rev. 97(6):2243-66 (1997).
Ishida et al., "N-formylation of amines via the aerobic oxidation of methanol over supported gold nanoparticles," ChemSusChem. 2(6):538-41 (2009).
Joyner et al., "A study of the adsorption of oxygen on silver at high pressure by electron spectroscopy," Chem Phys Lett. 60(3):459-62 (1979).
Klitgaard et al., "Oxidations of amines with molecular oxygen using bifunctional gold-titania catalysts," Green Chem. 10:419-23 (2008).
Liu et al., "Surface-mediated self-coupling of ethanol on gold," J Am Chem Soc. 131(16):5757-9 (2009).
Liu et al., "Unraveling molecular transformations on surfaces: a critical comparison of oxidation reactions on coinage metals," Chem Soc Rev. 37(10):2243-61 (2008).
Madix et al., "Anticipating catalytic oxidation reactions on gold at high pressure (including liquid phase) from ultrahigh vacuum studies," J Catal. 258:410-413 (2008).
Min et al., "Efficient CO oxidation at low temperature on Au(111)," J Phys Chem B. 110(40):19833-8 (2006).
Mo et al., "Selective production of hydrogen from partial oxidation of methanol over silver catalysts at low temperatures," Chem Commun (Camb). (12):1426-7 (2004).
Nordstrom et al., "Amide synthesis from alcohols and amines by the extrusion of dihydrogen," J Am Chem Soc. 130(52):17672-3 (2008).
Pestryakov et al., "Alcohol selective oxidation over modified foam-silver catalysts," Catalysis Today. 91-92C:49-52 (2004).
R.J. Madix and J.T. Roberts, Surface Reactions: Springer Series in Surface Science vol. 34; Springer: Berlin, 1994.
Ramalingan et al., "Mercury-catalyzed rearrangement of ketoximes into amides and lactams in acetonitrile," J Org Chem. 72(12):4536-8 (2007).
Saxon et al., "Cell surface engineering by a modified Staudinger reaction," Science. 287(5460):2007-10 (2000).

(Continued)

*Primary Examiner* — Shailendra Kumar
(74) *Attorney, Agent, or Firm* — Clark & Elbing LLP; Kristina Bicker-Brady

(57) ABSTRACT

The invention provides a method for producing amides via the reaction of aldehydes and amines with oxygen adsorbed on a metallic silver or silver alloy catalyst. An exemplary reaction is shown in Scheme 1: (I), (II), (III).

Scheme 1.

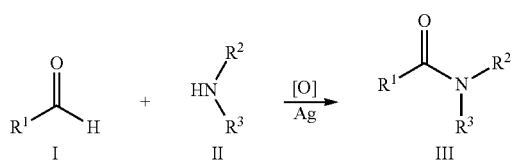

13 Claims, 2 Drawing Sheets

(56) References Cited

OTHER PUBLICATIONS

Seo et al., "Mild amidation of aldehydes with amines mediated by lanthanide catalysts," Org Lett. 10(2):317-9 (2008).
Shimizu et al., "Direct dehydrogenative amide synthesis from alcohols and amines catalyzed by gamma-alumina supported silver cluster," Chem. Eur. J. 15(39):9977-80 (2009).
Thornburg et al., "Cleavage of N-H bonds by active oxygen on Ag(110) I. Ammonia," Surf Sci. 220:268-94 (1989).
Thornburg et al., "Cleavage of NH bonds by active oxygen on Ag(110) II. Selective oxidation of ethylamine to acetonitrile," Surf Sci. 226:61-76 (1990).
Uenoyama et al., "Alkyne carbonylation by radicals: tin-radical-catalyzed synthesis of alpha-methylene amides from 1-alkynes, carbon monoxide, and amines," Angew Chem Int Ed Engl. 44(7):1075-8 (2005).
Wachs et al., "The oxidation of methanol on a silver (110) catalyst," Surf Sci. 76:531-558 (1978).
Watson et al., "Ruthenium-catalyzed oxidation of alcohols into amides," Org Lett. 11(12):2667- 70 (2009).
Xu et al., "Highly selective acylation of dimethylamine mediated by oxygen atoms on metallic gold surfaces," Angew Chem Int Ed Engl. 49(2):394-8 (2010).
Xu et al., "Selectivity control in gold-mediated esterification of methanol," Angew Chem Int Ed Engl. 48(23):4206-9 (2009).
Yoo et al., "Highly efficient oxidative amidation of aldehydes with amine hydrochloride salts," J Am Chem Soc. 128(40):13064-5 (2006).
International Search Report and Written Opinion for International Patent Application No. PCT/2011/022434, mailed May 31, 2011 (12 pages).

\* cited by examiner

SILVER-CATALYZED SYNTHESIS OF AMIDES FROM AMINES AND ALDEHYDES

STATEMENT AS TO GOVERNMENT SPONSORED RESEARCH

This invention was made with U.S. government support under National Science Foundation awards CHE-0513936, PHY-0646094, CHE-0545335, DMR-0820484 and Department of Energy award DE-FG02-84ER13289. The U.S. Government has certain rights in the invention.

CROSS-REFERENCE TO RELATED APPLICATIONS

This application is the National Stage of International Application No. PCT/US2011/022434, filed Jan. 25, 2011, which claims benefit of U.S. Provisional Application No. 61/336,673, filed Jan. 25, 2010, which is hereby incorporated by reference.

FIELD OF THE INVENTION

The invention is in the field of synthetic organic chemistry, and relates specifically to chemical processes involving catalysis, oxidation, and amide synthesis.

BACKGROUND OF THE INVENTION

Amidation is a fundamentally important synthetic process in chemistry and biology. The amide group, an important motif in natural products, polymers, and pharmaceuticals, may be introduced by reactions of carboxylic acids or their derivatives with amines, modified Staudinger reactions, aminocarbonylation of halides with CO and amines, rearrangements of ketoximes and aldoximes, and transition-metal-catalyzed carbonylation of alkenes and alkynes with amines. These processes frequently involve complex procedures and costly or hazardous reagents, and may produce toxic chemical waste.

The direct oxidative synthesis of amides via catalyzed reactions of amines with alcohols or aldehydes has recently attracted interest, because of the environmentally-benign nature of the reactions and the wide availability of the starting materials. A few homogeneous transition metal complexes have been reported to catalyze this class of reactions effectively, although the mechanistic details of the reactions remain unclear. (D. Gunanathan et al., *Science* 2007, 317, 790; L. U. Nordstrøm et al., *J. Am. Chem. Soc.* 2008, 130, 17672; W. Yoo, and C Li, *J. Am. Chem. Soc.* 2006, 128, 13064; S. Y. Seo and T. J. Marks, *Org. Lett.* 2008, 10, 317.)

For industrial-scale syntheses, heterogeneous catalysts are much preferred, and recent studies of supported gold and silver catalysts in the direct synthesis of amides suggest that heterogeneous processes may be possible. (S. K. Klitgaard et al., *Green Chem.* 2008, 10, 419; T. Ishida and M. Haruta, *Chemsuschem* 2009, 2, 538; K. Shimizu et al., *Chem. Eur. J.* 2009, 15, 9977.)

The prior art processes for this transformation are handicapped by certain disadvantages, such as high pressures, high temperatures, organic by-products, and soluble and/or expensive catalysts. There remains a need for efficient, cost-effective, heterogeneous catalytic syntheses of amides.

SUMMARY OF THE INVENTION

The invention provides a method for preparing an amide by contacting an aldehyde and an amine (e.g., a primary or secondary amine) with oxygen absorbed on a metallic silver catalyst. In one embodiment, an amide of formula III is prepared by contacting an aldehyde of formula I and an amine of formula II with oxygen adsorbed on a metallic silver catalyst, as shown in Scheme 1.

Scheme 1

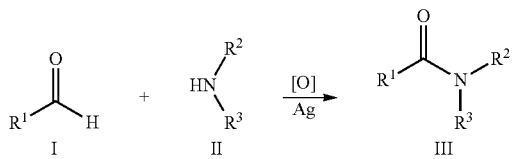

The metallic silver may optionally be modified by alloying with other metals. In the structures shown, $R^1$ may be H, $C_1$-$C_6$ straight chain alkyl, $C_3$-$C_6$ branched alkyl, or $C_3$-$C_8$ cycloalkyl; and $R^2$ and $R^3$ may each independently be H, $C_1$-$C_6$ straight chain alkyl, $C_3$-$C_6$ branched alkyl, or $C_3$-$C_8$ cycloalkyl. Cyclic amines may also be employed, where $R^2$ and $R^3$, together with the nitrogen to which they are attached, form a 3- to 6-membered heterocyclic ring, such as a pyrrolidine, piperidine, or morpholine ring. In addition, the amide and amine may be unimolecular, e.g., where $R^1$ and $R^2$ combine to form $C_1$-$C_6$ alkylene. In one example, $R^1$ is H, $C_1$-$C_4$ straight chain alkyl, $C_3$-$C_4$ branched alkyl, or $C_3$-$C_4$ cycloalkyl; and $R^2$ and $R^3$ are each independently be H, $C_1$-$C_4$ straight chain alkyl, $C_3$-$C_4$ branched alkyl, or $C_3$-$C_4$ cycloalkyl, each of which may be unsubstituted or substituted as described herein. The process can take place at moderate temperatures (250-350 K), does not require pressurization, and, under optimum conditions, produces water as the sole by-product.

In one embodiment, the silver alloy is an alloy of silver and gold. The catalyst is, for example, carried on an inert supporting material. In other embodiments, the source of the adsorbed oxygen is oxygen gas. In certain embodiments, $R^2$ and $R^3$ are methyl. An exemplary aldehyde is formaldehyde. As defined herein, substituents on the amine or aldehyde may be substituted or unsubstituted. The amine and aldehyde may or may not be further substituted with aldehyde or amino groups.

In certain embodiments, the amine is a primary amine. In other embodiments, the amine is a secondary amine. The catalyst may be promoted by a material selected from the group consisting of metal halides, carbonates, sulfites, sulfates, nitrites, and nitrates, transition metal oxoanions, lanthanides, and alkali and alkaline earth metals. The temperatures is, for example, from 270 to 1000 K. The pressure is, for example, from 0.1 atm to 5 atmospheres.

Other features and advantages will be apparent from the following description, drawings, and the claims.

DEFINITIONS

The term "alkyl," as used herein, is inclusive of substituted and unsubstituted straight chain and branched chain saturated groups from 1 to 6 carbons, unless otherwise specified. Alkyl groups can be saturated or unsaturated and are exemplified by methyl, ethyl, n- and iso-propyl, n-, sec-, iso- and tert-butyl, neopentyl, ethenyl, 1-propenyl, 2-propenyl, 2-methyl-1-propenyl, 1-butenyl, 2-butenyl, ethynyl, 1-propynyl, and the like and may be optionally substituted with one, two, three, or, in the case of alkyl groups of two carbons or more, four substituents independently selected from the group consisting of:

alkoxy; amino; aryl; aryloxy; alkaryloxy; cycloalkyl; cycloalkyloxy; halo; heterocyclyl; (heterocyclyl)oxy; hydroxyl (—OH); oxo (=O); thioalkoxy; thiol (—SH); —CO$_2$R$^A$, where R$^A$ is selected from the group consisting of (a) alkyl, (b) aryl, (c) hydrogen, and (d) alkaryl; —C(O)NR$^B$R$^C$, where each of R$^B$ and R$^C$ is, independently, selected from the group consisting of (a) hydrogen, (b) alkyl, (c) aryl, and (d) alkaryl. In some embodiments, each of these substituent groups can be further substituted as described herein.

The term "alkaryl," as used herein, represents an aryl group, as defined herein, attached to the parent molecular group through an alkylene group. Exemplary unsubstituted alkaryl groups are from 7 to 16 carbons, e.g., where the alkylene group is C$_1$-C$_6$ and the aryl portion is C$_6$-C$_{10}$. In some embodiments, the alkylene and the aryl each can be further substituted with 1, 2, 3, or 4 substituent groups as defined herein for the respective groups.

The term "alkcycloalkyl" represents a cycloalkyl group, as defined herein, attached to the parent molecular group through an alkylene group.). Exemplary unsubstituted alkcycloalkyl groups are from 4 to 14 carbons, e.g., where the alkylene group is C$_1$-C$_6$ and the cycloalkyl portion is C$_3$-C$_8$. In some embodiments, the alkylene and the cycloalkyl each can be further substituted with 1, 2, 3, or 4 substituent groups as defined herein for the respective group.

The term "alkheterocyclyl" represents a heterocyclyl group, as defined herein, attached to the parent molecular group through an alkylene group, as defined herein. Exemplary unsubstituted alkheterocyclyl groups are from 4 to 14 carbons, e.g., where the alkylene group is C$_1$-C$_6$ and the heterocyclyl portion is C$_3$-C$_8$. In some embodiments, the alkylene and the heterocyclyl each can be further substituted with 1, 2, 3, or 4 substituent groups as defined herein for the respective group.

The term "alkoxy" represents a chemical substituent of formula —OR, where R is a C$_{1-6}$ alkyl group, unless otherwise specified. In some embodiments, the alkyl group can be further substituted with 1, 2, 3, or 4 substituent groups as defined herein.

The term "amino," as used herein, represents -N(R$^{N1}$)$_2$, wherein each R$^{N1}$ is, independently, H, OH, an N-protecting group, alkyl, alkoxy, aryl, alkaryl, cycloalkyl, alkcycloalkyl, heterocyclyl, alkheterocyclyl, or two R$^{N1}$ combine to form a heterocyclyl or an N-protecting group.

The term "alkylene" and "alk," as used herein, represent a saturated or unsaturated divalent hydrocarbon group derived from a straight or branched chain saturated hydrocarbon by the removal of two hydrogen atoms, and is exemplified by methylene, ethylene, isopropylene, and the like. In some embodiments, the alkylene can be further substituted with 1, 2, 3, or 4 substituent groups as defined herein for an alkyl group.

The term "aryl," as used herein, represents a mono-, bicyclic, or multicyclic carbocyclic ring system having one aromatic ring and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: alkyl; alkoxy; aryl; amino; alkaryl; cycloalkyl; alkcycloalkyl; halo; heterocyclyl; (heterocyclyl)oxy; hydroxyl (—OH); thioalkoxy; —(CH$_2$)$_q$CO$_2$R$^A$, where q is an integer from zero to four, and R$^A$ is selected from the group consisting of (a) alkyl, (b) aryl, (c) hydrogen, and (d) alkaryl; —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) alkaryl; thiol (—SH); aryloxy; cycloalkoxy; alkaryloxy; and alkheterocyclyl. In some embodiments, each of these groups can be further substituted as described herein.

The term "alkaryloxy," as used herein, represents an alkaryl group, as defined herein, attached to the parent molecular group through an oxygen atom. In some embodiments, the alkaryl group can be substituted with 1, 2, 3, or 4 substituents as defined herein.

The term "aryloxy" represents an aryl group, as defined herein, attached to the parent molecular group through an oxygen atom. In some embodiments, the aryl group can be substituted with 1, 2, 3, or 4 substituents as defined herein.

The term "cycloalkyl," as used herein represents a monovalent saturated or unsaturated non-aromatic cyclic hydrocarbon group from three to eight carbons, unless otherwise specified. Cycloalkyl groups may be saturated or unsaturated and are exemplified by cyclopropyl, cyclobutyl, cyclopentyl, cyclohexyl, cycloheptyl, bicyclo[2.2.1.]heptyl, cyclopentenyl, cyclohexenyl, and the like. Cycloalkyl groups may be saturated or unsaturated. The cycloalkyl groups of this invention can be optionally substituted with: alkyl; alkoxy; aryl; amino; alkaryl; cycloalkyl; alkcycloalkyl; halo; heterocyclyl; (heterocyclyl)oxy; hydroxyl (—OH); thioalkoxy; —(CH$_2$)$_q$CO$_2$R$^A$, where q is an integer from zero to four, and R$^A$ is selected from the group consisting of (a) alkyl, (b) aryl, (c) hydrogen, and (d) alkaryl; —(CH$_2$)$_q$CONR$^B$R$^C$, where q is an integer from zero to four and where R$^B$ and R$^C$ are independently selected from the group consisting of (a) hydrogen, (b) alkyl, (c) aryl, and (d) alkaryl; thiol (—SH); aryloxy; cycloalkoxy; alkaryloxy; alkheterocyclyl; and oxo (C=O).

The term "cycloalkoxy," as used herein, represents a cycloalkyl group, as defined herein, attached to the parent molecular group through an oxygen atom. In some embodiment, the cycloalkyl group can be further substituted with 1, 2, 3, or 4 substituent groups as described herein.

The term "halo," as used herein, represents a halogen selected from bromine, chlorine, iodine, or fluorine.

The term "heterocyclyl," as used herein represents a 3-, 4-, 5- or 6-membered ring, unless otherwise specified, containing one, two, three, or four heteroatoms independently selected from the group consisting of nitrogen, oxygen, and sulfur. The 5-membered ring has zero to two double bonds, and the 6-membered rings have zero to three double bonds. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring, such as indolyl, quinolyl, isoquinolyl, tetrahydroquinolyl, benzofuryl, benzothienyl and the like. Examples of fused heterocyclyls include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, isoindazoyl, triazolyl, tetrazolyl, oxadiazolyl, purinyl, thiadiazolyl, tetrahydrofuranyl, dihydrofuranyl, tetrahydropyranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, oxepanyl, thiepanyl, azocanyl, oxecanyl, thiocanyl, and the like. Any of the heterocyclyl groups mentioned herein may be optionally substituted with one, two, three, four or substituents independently selected from the group consisting of: alkyl; alkoxy; aryl; amino; alkaryl; cycloalkyl; alkcycloalkyl; halo; heterocyclyl; (heterocyclyl)oxy; hydroxyl (—OH); thioalkoxy; —$(CH_2)_qCO_2R^A$, where q is an integer from zero to four, and $R^A$ is selected from the group consisting of (a) alkyl, (b) aryl, (c) hydrogen, and (d) alkaryl; —$(CH_2)_q$ $CONR^BR^C$, where q is an integer from zero to four and where $R^B$ and $R^C$ are independently selected from the group consisting of (a) hydrogen, (b) alkyl, (c) aryl, and (d) alkaryl; thiol (—SH); aryloxy; cycloalkoxy; alkaryloxy; alkheterocyclyl; and oxo (C=O). In some embodiments, each of these groups can be further substituted as described herein.

The term "(heterocyclyl)oxy," as used herein, represents a heterocyclyl group, as defined herein, attached to the parent molecular group through an oxygen atom. In some embodiments, the heterocyclyl group can be substituted with 1, 2, 3, or 4 substituent groups as defined herein.

The term "N-protecting group," as used herein, represents those groups intended to protect an amino group against undesirable reactions during synthetic procedures. Commonly used N-protecting groups are disclosed in Greene, "Protective Groups in Organic Synthesis," 3$^{rd}$ Edition (John Wiley & Sons, New York, 1999), which is incorporated herein by reference. N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, alkaryl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "thioalkoxy," as used herein, represents an alkyl group, as defined herein, attached to the parent molecular group via a sulfur atom. In some embodiments, the alkyl group can be further substituted with 1, 2, 3, or 4 substituent groups as described herein.

DETAILED DESCRIPTION OF THE INVENTION

Figure 1:
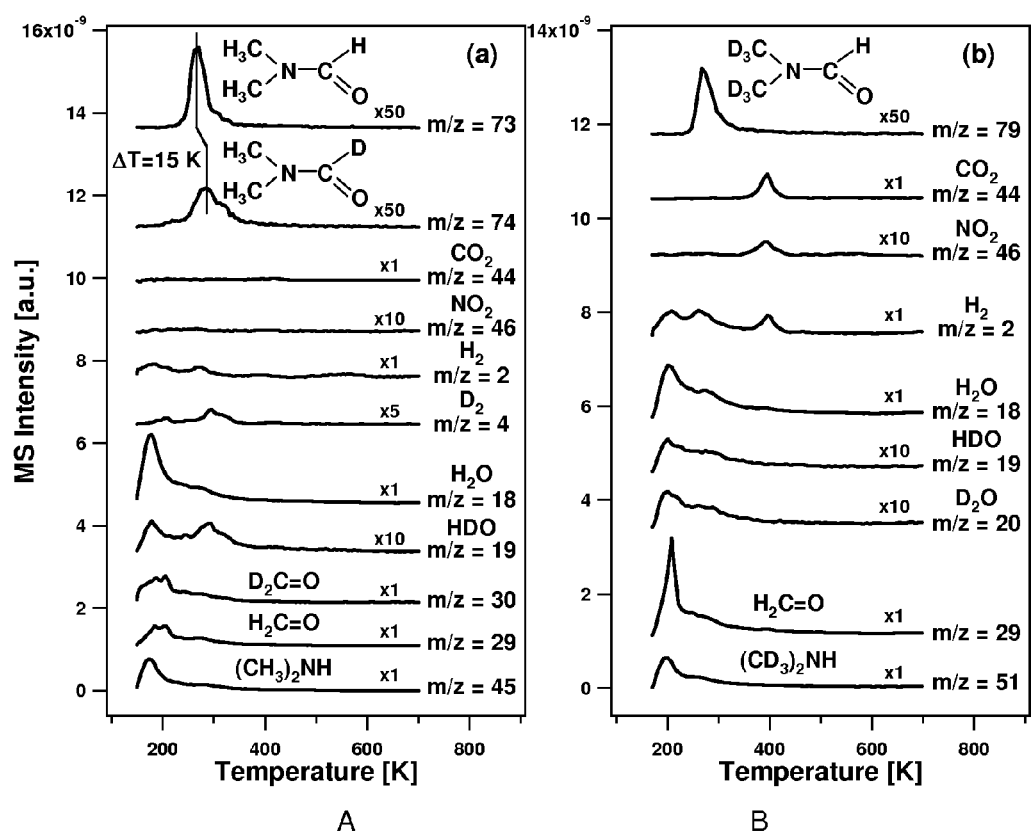
FIG. 1 shows TPRS data from the mass spectrometric detection of products as a function of temperature, during the heating of dimethylamine and a mixture of $d_0$- and $d_2$-formaldehyde on 0.1 monolayer oxygen-covered Ag(111) at 140 K (FIG. 1A), and $d_6$-dimethylamine and formaldehyde on 0.1 monolayer oxygen-covered Ag(111) starting at 170 K (FIG. 1B).

The invention provides a process for the heterogeneous catalytic, oxygen-assisted acylation of primary or secondary organic amines to form amides, using metallic silver or silver alloys as the catalyst, and an aldehyde as the source of the acyl group.

The present inventors have now discovered that oxygen adsorbed on silver is also capable of accomplishing the oxidative coupling of aldehydes and amines to form amides. The effectiveness of silver as a catalyst for this transformation is unexpected, because there is no indication in the prior art that such coupling reactions might be possible on metallic silver. Previously, the present inventors demonstrated that the cross-coupling of dimethylamine and formaldehyde on gold single crystal surfaces proceeds via the initial selective activation of the RR'N—H bond by adsorbed oxygen and the subsequent nucleophilic attack of the adsorbed nucleophile (RR'N$^-$) on the electron-deficient aldehydic carbon. (B. Xu, L. Zhou, R. J. Madix, C. M. Friend, *Angew. Chem. Int. Ed. Engl.*, 2010, 49, 394-398.) Oxygen adsorbed on silver has been shown to activate alcohols and amines (X. Liu, R. J. Madix, C. M. Friend, *Chem. Soc. Rev.* 2008, 37, 2243; I. E. Wachs, R. J. Madix, *Surf. Sci.* 1978, 76, 531; D. M. Thornburg, R. J. Madix, *Surf. Sci.* 1990, 226, 61; J. L. Gong, T. Yan, C. B. Mullins, *Chem. Commun.* 2009, 761).

The scope of the present invention is not limited to any particular reaction mechanism(s), and the present inventors do not intend to be limited by mechanistic theories. Accordingly, the following discussion is presented only to stimulate further thoughts on the process. It is known that oxygen dissociates on silver surfaces to form chemisorbed oxygen with controllable coverage. (R. J. Madix and J. T. Roberts, *Surface Reactions: Springer Series in Surface Science* Vol. 34; Springer: Berlin, 1994.) Such oxygenated surfaces are known to activate the N—H bond in ammonia and amines. (D. M. Thornburg and R. J. Madix, *Surf Sci.* 1990, 226, 61; Idem, ibid., 1989, 220, 268.) The first reaction step is oxidative deprotonation of the amine to form an adsorbed amide anion (e.g., $R^2R^3N^-_{(a)}$) and water. Nucleophilic attack, e.g., by $R^2R^3N^-_{(a)}$, on the aldehydic carbon of the aldehyde forms an adsorbed hemiaminal intermediate, e.g., [$R^2R^3NC(H)(R^1)$ $O^-_{(a)}$], on the surface. A subsequent β-hydride elimination is the rate-limiting step for the formation of the amide, as indicated by the kinetic isotope effect mentioned above.

The selective catalytic action of metallic silver originates in the selective reactivity of adsorbed oxygen with the N—H bond in the amine, and the nucleophilic reactivity of the resulting adsorbed amide toward the carbonyl carbon in the aldehyde. This is a general feature of the reaction and is independent of the exact identities of the amine and aldehyde.

A preferred metal for use in alloys is gold, for example as described in U.S. Pat. No. 4,219,509, the contents of which are incorporated herein by reference in their entirety. The metallic silver or silver alloy may be used in bulk form, such as granules or a gauze, or it may be carried on an inert supporting material. The silver-catalyzed partial oxidation of methanol to formaldehyde is an industrial process of considerable importance, and for this reason a wide variety of supports for silver catalysts, and methods for depositing metallic silver thereon, are known in the art. (See H. F. Rase, *Handbook of Commercial Catalysts: Heterogeneous Catalysts*, 2000, CRC Press, p. 283.) Suitable supports include but are not limited to ceramics and other refractory materials, such as alumina, silica, titania, and other metal oxides, and combinations thereof. Metallic supports in various forms (e.g., foils, foams, and wires in various woven and non-woven forms), plated with silver, may also be employed.

The catalyst may be unpromoted or may optionally be promoted by with additives and modifiers known in the art, including but not limited to metal halides, carbonates, sulfites, sulfates, nitrites, and nitrates; transition metal oxoanions, lanthanides, and alkali and alkaline earth metals. Examples of modified, supported silver catalysts are described in L. Mo et al., *Chem. Commun.*, 2004, 12, 1426-1427; A. N. Pestryakov, N. E. Bogdanchikovab and A. Knop-Gerickea, *Catalysis Today*, 2004, 91-92: 49-52; and references therein.

The process of the invention may be conducted either in the gas phase or in liquid solution. The reaction proceeds in the presence of oxygen adsorbed to the catalyst surface. The adsorbed oxygen originates from an oxygen source; suitable sources include but are not limited to added $O_2$, ozone (R. W. Joyner and M. W. Roberts, *Chem. Phys. Lett.*, 1979, 60, 459-462; B. K. Min et al., *J. Phys. Chem. B.* 2006, 110, 19833), $NO_2$ (S. R. Bare et al., *Surf. Sci.*, 1995, 342, 185-198), and other known oxygen sources, or mixtures thereof. Molecular oxygen may be derived from the ambient atmosphere.

The selectivity towards catalytic amidation of amines by aldehydes can be modified through control of the oxygen coverage and the reaction temperature. For greatest selectivity, low concentrations of oxygen are preferred. The reaction is not restricted to specific crystal planes of silver, and silver in bulk, polycrystalline, or particulate forms is suitable as a catalyst.

The use of the method of the invention in continuous synthesis is exemplified by the following procedure: A rolled silver gauze is placed into a column, and a mixture of oxygen and an inert gas is fed through the column. The pressure and concentration of oxygen are adjusted so as to produce between 0.1 and 0.25 ML coverage of the exposed silver surface. An amine and an aldehyde, in approximately equimolar concentrations, may be added to a gas stream and allowed to flow through a column. The temperature, pressure, and concentrations of oxygen, amine, and aldehyde may be adjusted to optimize the yield and selectivity of the process. Temperatures may range from 270 to 1000 K, and pressures may range from 0.1 atm to several atmospheres.

By way of example, we describe below the highly selective oxygen-assisted amidation of dimethylamine with formaldehyde, mediated by metallic silver. The desired product, N,N-dimethylformamide, was formed on both Ag(111) and Ag(110) surfaces with nearly 100% selectivity in the presence of oxygen. The examples establish the general predictive nature of the reaction, and the roles of oxygen as oxidant and silver as catalyst.

EXAMPLES

The reactions were conducted by sequentially contacting dimethylamine and formaldehyde with silver surfaces that had been pre-covered with a partial monolayer (ML) of oxygen. Reaction progress and products were monitored by Temperature Programmed Reaction Spectroscopy (TPRS). In order to identify products unequivocally and to clarify the reaction mechanism, deuterated formaldehyde and dimethylamine were employed. FIG. 1A shows the results of temperature-programmed reaction of dimethylamine with a mixture of $d_0$- and $d_2$-formaldehyde (1.8:1 molar ratio) on 0.1 ML (10% of a monolayer) oxygen-covered Ag(111) at 140 K. The heating rate was approximately 5 K/s. N,N-dimethylformamide $(CH_3)_2NC(H)\!\!=\!\!O$ (m/z 73) was formed along with $H_2$ (m/z 2) and $H_2O$ (m/z 18) at ca. 270 K, whereas $d_1$-N,N-dimethylformamide $(CH_3)_2NC(D)\!\!=\!\!O$ (m/z 74) was produced along with $D_2$ (m/z 4) and HDO (m/z 18) at ca. 285 K. N,N-dimethylformamide was identified by quantitative comparison of the mass fragmentation pattern of the product to that obtained from a reference sample condensed on a clean surface. There was no detectable combustion (no $CO_2$, m/z 44 or $NO_2$, m/z 46), nor were other secondary oxidation products detected, and no residual carbon or nitrogen species were detected on the surface after the reaction by X-ray photoelectron spectroscopy. The method of the invention is thus capable of producing N,N-dimethylformamide with 100% selectivity.

Reaction of $d_6$-dimethylamine $((CD_3)_2NH)$ with formaldehyde on a silver surface yielded $d_6$-N,N-dimethylformamide $((CD_3)_2NC(H)\!\!=\!\!O)$ at ca. 270 K, as indicated by the mass shift of the parent ion from 73 to 79 amu and the corresponding mass shifts of the primary mass fragments (FIG. 1B). The isotopic reactions showed that the methyl groups in dimethylamine and the carbonyl in formaldehyde were preserved, and that the only C—H bond breaking event was the cleavage of the aldehydic C—H bond. Notably, $(CH_3)_2NC(D)\!\!=\!\!O$ evolved at a temperature ca. 15 K higher than did $(CH_3)_2NC(H)\!\!=\!\!O$ and $(CD_3)_2NC(H)\!\!=\!\!O$. This is a clear indication of a kinetic isotope effect, suggesting that aldehydic C—H bond breaking is the rate-limiting step in amide formation. The production of hydrogen and water simultaneously with release of the amide strongly supports an adsorbed hemiaminal intermediate, $(CH_3)_2NC(H_2)O_{(a)}$, as the immediate precursor of the amide.

In addition to the $d_6$-N,N-dimethylformamide, combustion products, $CO_2$, $NO_2$, and $H_2$ were also formed at ca. 400 K in the reaction of $d_6$-dimethylamine and formaldehyde on 0.1 ML O-covered Ag(111) at 170 K. These products appear to be formed via direct oxidation of dimethylamine and formaldehyde, as they also appear at identical temperatures in the oxidation of dimethylamine or formaldehyde on O-covered Ag(111).

Figure 2:
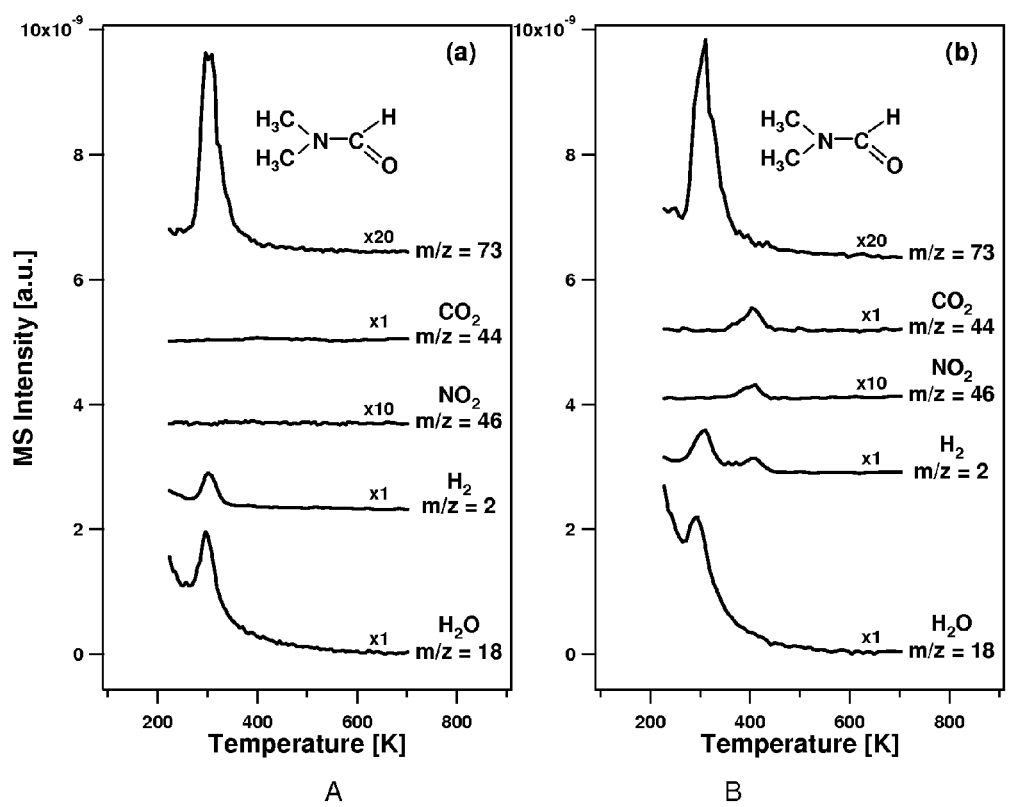
FIG. 2 shows TPRS data from the mass spectrometric detection of products as a function of temperature, during the heating of dimethylamine and formaldehyde on 0.25 monolayer oxygen-covered Ag(110) (FIG. 2A), and 0.5 monolayer oxygen-covered Ag(110) (FIG. 2B), starting at 120 K.

N,N-dimethylformamide was also formed with ca. 100% selectivity in the reaction of dimethylamine and formaldehyde on a 0.25 ML O-covered Ag(110) surface at 120 K, along with hydrogen and water (FIG. 2A). When the oxygen coverage was increased to 0.5 ML, combustion products, $CO_2$, $NO_2$, and $H_2$ were formed in addition to N,N-dimethylformamide, indicating a reduced selectivity towards amidation (FIG. 2B). Similar trends are observed in the self-coupling of alcohols and cross-coupling of dimethylamine and formaldehyde on gold single crystal surfaces. (B. Xu et al., *Angew. Chem., Int. Ed.* 2009, 48, 1; X. Liu et al., *J. Am. Chem. Soc.* 2009, 131, 5757; B. Xu, L. Zhou, R. J. Madix, C. M Friend, *Angew. Chem. Int. Ed. Engl.*, 2010, 49, 394-398.)

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A method for preparing an amide comprising reacting an aldehyde and a primary or secondary amine with oxygen adsorbed on a catalyst comprising silver metal or an alloy thereof to produce the amide.

2. The method of claim 1, wherein the amide is of formula III, the aldehyde is of formula I and the primary or secondary amine is of formula II:

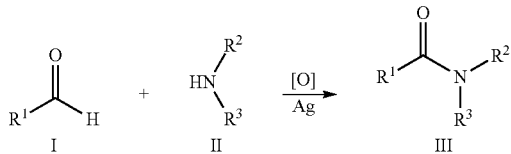

wherein $R^1$ is selected from the group consisting of H, $C_1$-$C_6$ straight chain alkyl, $C_3$-$C_6$ branched alkyl, and $C_3$-$C_8$ cycloalkyl; and wherein $R^2$ and $R^3$ are independently selected from the group consisting of H, $C_1$-$C_6$ straight chain alkyl, $C_3$-$C_6$ branched alkyl, and $C_3$-$C_8$ cycloalkyl, or $R^2$ and $R^3$, together with the nitrogen to which they are attached, form a 3- to 6-membered heterocyclic ring; or $R^1$ and $R^2$ together are $C_1$-$C_6$ alkylene.

3. The method of claim 2, wherein $R^1$ is selected from the group consisting of H, $C_1$-$C_4$ straight chain alkyl, $C_3$-$C_4$ branched alkyl, and $C_3$-$C_4$ cycloalkyl; and wherein $R^2$ and $R^3$ are independently selected from the group consisting of H, $C_1$-$C_4$ straight chain alkyl, $C_3$-$C_4$ branched alkyl, and $C_3$-$C_4$ cycloalkyl, or $R^2$ and $R^3$, together with the nitrogen to which they are attached, form a 3- to 6-membered heterocyclic ring.

4. The method of claim 2, wherein $R^2$ and $R^3$ are methyl.

5. The method of claim 1, wherein the aldehyde is formaldehyde.

6. The method of claim 1, wherein the silver alloy is an alloy of silver and gold.

7. The method of claim 1, wherein the source of the adsorbed oxygen is oxygen gas.

8. The method of claim 1, wherein the amine is a primary amine.

9. The method of claim 1, wherein the amine is a secondary amine.

10. The method of claim 1, wherein the catalyst is promoted by a material selected from the group consisting of metal halides, carbonates, sulfites, sulfates, nitrites, and nitrates, transition metal oxoanions, lanthanides, and alkali and alkaline earth metals.

11. The method of claim 1, wherein the temperatures is from 270 to 1000 K.

12. The method of claim 1, wherein the pressure is from 0.1 atm to 5 atmospheres.

13. The method of claim 1, wherein the catalyst is carried on an inert supporting material.

* * * * *